United States Patent [19]

Wagner et al.

[11] Patent Number: 5,461,069
[45] Date of Patent: Oct. 24, 1995

[54] SUBSTITUTED AZA(CYCLO)ALKANES

[75] Inventors: Klaus Wagner, Bergisch Gladbach; Christoph Erdelen; Jürgen Hartwig, both of Leichlingen; Wolfgang Leicht, Leverkusen; Wilhelm Stendel, Wuppertal, all of Germany

[73] Assignee: Bayer Aktiengesellschaft, Leverkusen, Germany

[21] Appl. No.: 139,350

[22] Filed: Oct. 20, 1993

[30] Foreign Application Priority Data

Oct. 27, 1992 [DE] Germany ............ 42 36 204.0

[51] Int. Cl.$^6$ .................. C07D 403/06; A01N 43/40
[52] U.S. Cl. .................. 514/341; 514/365; 546/278; 546/22; 548/112; 548/202; 548/203; 548/205
[58] Field of Search .................. 546/330, 332, 546/278, 22; 514/357, 341, 365; 548/202, 203, 205, 112

[56] References Cited

U.S. PATENT DOCUMENTS

| 4,849,432 | 7/1989 | Shiokawa et al. ............ 514/341 |

FOREIGN PATENT DOCUMENTS

| 0381130 | 8/1980 | European Pat. Off. ............ 546/330 |
| 0192060 | 8/1986 | European Pat. Off. ............ 514/341 |
| 0302339 | 2/1989 | European Pat. Off. ............ 546/332 |
| 0386565 | 9/1990 | European Pat. Off. ............ 514/341 |
| 0425978 | 5/1991 | European Pat. Off. ............ 514/341 |
| 0455000 | 11/1991 | European Pat. Off. ............ 514/341 |
| 0471372 | 2/1992 | European Pat. Off. ............ 514/341 |
| 0483052 | 4/1992 | European Pat. Off. ............ 514/341 |
| 0547557 | 6/1993 | European Pat. Off. ............ 514/341 |
| 9104965 | 4/1991 | WIPO ............ 514/341 |

*Primary Examiner*—Alan L. Rotman
*Assistant Examiner*—Zinna N. Davis
*Attorney, Agent, or Firm*—Sprung Horn Kramer & Woods

[57] ABSTRACT

Insecticidally active substituted aza(cyclo)alkanes of the formula (I)

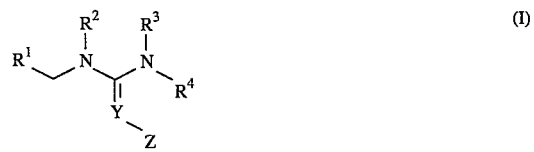

in which

R$^1$ represents a five- or six-membered heterocyclic grouping which contains 1, 2, 3 or 4 nitrogen atoms and/or one or two oxygen atoms or sulphur atoms as the heteroatom ring members—the number of heteroatoms being 1, 2, 3 or 4—and which is optionally substituted R$^2$ represents hydroxyalkyl, polyhydroxyalkyl, alkoxyalkyl or polyalkoxyalkyl, R$^3$ represents hydrogen, alkyl, hydroxyalkyl, dihydroxyalkyl, alkoxyalkyl or dialkoxyalkyl, R$^4$ represents hydrogen or any of various organic radicals, Y represents nitrogen or a CH group and Z represents cyano or nitro.

Also intermediates therefor and process of making.

5 Claims, No Drawings

SUBSTITUTED AZA(CYCLO)ALKANES

The invention relates to novel substituted aza(cyclo)alkanes, processes for their preparation and their use as agents for combating pests, in particular as insecticides.

It is already known that certain heterocyclic compounds possess insecticidal properties (cf. EP-A 192 060).

The novel substituted aza(cyclo)alkanes of the general formula (I) have now been found

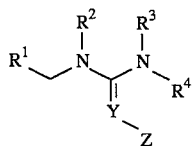

in which
- $R^1$ represents a five-or six-membered heterocyclic grouping, which contains 1, 2, 3 or 4 nitrogen atoms and/or one or two oxygen atoms or sulphur atoms as the heteroatom ring members—the number of heteroatoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, arylthio, arylamino, aralkyl, formylamino, alkylcarbonylamino, formyl, carbamoyl, alkylcarbonyl and/or alkoxycarbonyl,
- $R^2$ represents hydroxyalkyl, polyhydroxyalkyl, alkoxyalkyl or polyalkoxyalkyl,
- $R^3$ represents hydrogen, alkyl, hydroxyalkyl, dihydroxyalkyl, alkoxyalkyl or dialkoxyalkyl,
- $R^2$ and $R^3$ together represent hydroxyalkanediyl, dihydroxyalkanediyl, alkoxyalkanediyl, dialkoxyalkanediyl, oxoalkanediyl or dioxoalkanediyl,
- $R^4$ represents hydrogen, alkyl (which is optionally substituted by halogen, cyano, alkoxy, alkylthio, dialkylamino, trialkylsilyl, alkoxycarbonyl, carboxyl, carbamoyl, alkylaminocarbonyl or dialkylaminocarbonyl, or by the radical $R^1$, where $R^1$ has the abovementioned meaning), alkenyl (which is optionally substituted by halogen), alkinyl, benzyl (which is optionally substituted by halogen, cyano, nitro, alkyl, halogenoalkyl, alkoxy or alkoxycarbonyl), formyl, alkylcarbonyl (which is optionally substituted by halogen, cyano, phenyl, phenoxy or alkoxy), cycloalkylcarbonyl (which is optionally substituted by halogen and/or alkyl), alkenylcarbonyl (which is optionally substituted by halogen), phenylcarbonyl or naphthylcarbonyl (which are optionally substituted by halogen, alkyl, halogenoalkyl, cyano, nitro, alkoxy and/or alkoxycarbonyl), alkoxycarbonyl, benzyloxycarbonyl, phenoxycarbonyl, alkylthiocarbonyl, benzylthiocarbonyl, phenylthiocarbonyl, alkylaminocarbonyl, dialkylaminocarbonyl, phenylaminocarbonyl (which is optionally substituted by halogen, cyano, nitro, alkyl, halogenoalkyl, alkoxy, halogenoalkoxy, alkylthio, halogenoalkylthio or alkoxycarbonyl), benzoylaminocarbonyl (which is optionally substituted by halogen, alkyl or halogenoalkyl), phenylsulphonylaminocarbonyl (which is optionally substituted by halogen, alkyl, halogenoalkyl, alkoxy, halogenoalkoxy or alkoxycarbonyl), alkylthio (which is optionally substituted by halogen), phenylthio (which is optionally substituted by halogen, nitro or alkyl), alkylsulphinyl, alkylsulphonyl (which is optionally substituted by halogen), phenylsulphinyl (which is optionally substituted by halogen, nitro or alkyl), phenylsulphonyl or naphthylsulphonyl (which are optionally substituted by halogen, cyano, nitro, alkyl, halogenoalkyl, alkoxy, halogenoalkoxy and/or alkoxycarbonyl), dialkyl(thio)phosphoryl, alkylalkoxy-(thio)phosphoryl or dialkoxy(thio)phosphoryl,
- Y represents nitrogen or a CH group and
- Z represents cyano or nitro.

The novel substituted aza(cyclo)alkanes of the general formula (I) are obtained if (a) azaalkanes of the general formula (II)

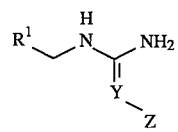

in which
$R^1$, Y and Z have the abovementioned meaning, are reacted with halogen compounds of the general formula (IIIa)

$$X-R^2 \qquad (IIIa)$$

and/or halogen compounds of the general formula (IIIb)

$$X-R^3 \qquad (IIIb)$$

in which
$R^2$ and $R^3$ have the abovementioned meaning and
X represents halogen, optionally in the presence of an acid acceptor, optionally in the presence of a catalyst or optionally in the presence of a diluent, or if (b) compounds of the general formula (I), in which $R^2$ or $R^3$ represents dialkoxyalkyl and $R^1$, $R^4$, Y and Z have the abovementioned meaning, are heated, optionally in the presence of a reaction aid and optionally in the presence of a diluent, or if (c) compounds of the general formula (I), in which $R^2$ and $R^3$ together represent oxoalkanediyl and $R^1$, $R^4$, Y and Z have the abovementioned meaning, are reacted with an hydrogenating agent, optionally in the presence of a reaction aid and optionally in the presence of a diluent, or if (d) compounds of the general formula (I), in which $R^2$ and $R^3$ together represent alkoxyalkanediyl or dialkoxyalkanediyl and $R^1$, $R^4$, Y and Z have the abovementioned meaning, are reacted with a hydrogen halide and/or an alkali metal halide as well as in the presence of diluents, or if (e) compounds of the general formula (I), in which $R^2$ and $R^3$ together represent hydroxyalkanediyl or dihydroxyalkanediyl and $R^1$, $R^4$, Y and Z have the abovementioned meaning, are reacted with an alkylating agent of the general formula (IV)

$$X^1-R \qquad (IV)$$

in which
R represents alkyl and
$X^1$ represents halogen or the grouping $-O-SO_2-O-R$ in which R has the abovementioned meaning, optionally in the presence of an acid binding agent and optionally in the presence of a diluent, or if (f) compounds of the general formula (I), in which $R^4$ represents hydrogen and $R^1$, $R^2$, $R^3$, Y and Z have the abovementioned meaning, are reacted with halogen compounds of the general formula (V)

$$X—R^4 \qquad (V)$$

in which

X represents halogen and $R^4$ has, with the exception of hydrogen, the abovementioned meaning, optionally in the presence of an acid acceptor and optionally in the presence of a diluent.

The novel substituted aza(cyclo)alkanes of the general formula (I) are distinguished by their high activity as insecticides.

The invention relates preferably to compounds of the formula (I) in which $R^1$ represents a five- to six-membered heterocyclic grouping from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, which is optionally substituted by fluorine, chlorine, bromine, iodine, cyano, nitro, $C_1$–$C_4$-alkyl (which is optionally substituted by fluorine and or chlorine), $C_2$–$C_4$-alkenyl (which is optionally substituted by fluorine and/or chlorine), $C_2$–$C_4$-alkinyl, $C_1$–$C_4$-alkoxy (which is optionally substituted by fluorine and/or chlorine), $C_3$–$C_4$-alkenyloxy (which is optionally substituted by fluorine and/or chlorine), $C_3$–$C_4$-alkinyloxy, $C_3$–$C_4$-alkylthio (which is optionally substituted by fluorine and/or chlorine), $C_3$–$C_4$-alkenylthio (which is optionally substituted by fluorine and/or chlorine), $C_3$–$C_4$-alkinylthio, $C_1$–$C_4$-alkylsulphinyl (which is optionally substituted by fluorine and/or chlorine), $C_1$–$C_4$-alkylsulphonyl (which is optionally substituted by fluorine and/or chlorine), amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkyl-carbonylamino, formyl, carbamoyl, $C_1$–$C_4$-alkylcarbonyl and/or $C_1$–$C_4$-alkoxy-carbonyl, $R^2$ represents $C_1$–$C_6$-hydroxyalkyl, dihydroxy-$C_1$–$C_6$-alkyl, $C_1$–$C_4$-alkoxy-$C_1$–$C_4$-alkyl or di-($C_1$–$C_4$-alkoxy)-$C_1$–$C_4$-alkyl, $R^3$ represents hydrogen, $C_1$–$C_6$-alkyl, $C_1$–$C_6$-hydroxyalkyl, dihydroxy-$C_1$–$C_6$-alkyl, $C_1$–$C_4$-alkoxy-$C_1$–$C_4$-alkyl or di-($C_1$–$C_4$-alkoxy)-$C_1$–$C_4$-alkyl, or $R^2$ and $R^3$ together represent hydroxy-$C_2$–$C_4$-alkanediyl, dihydroxy-$C_2$–$C_4$-alkanediyl, $C_1$–$C_4$-alkoxy-$C_2$–$C_4$-alkanediyl, di-($C_1$–$C_4$-alkoxy)-$C_2$–$C_4$-alkanediyl, oxo-$C_2$–$C_4$-alkanediyl or dioxo-$C_2$–$C_4$-alkanediyl, $R^4$ represents hydrogen, $C_1$–$C_4$-alkyl (which is optionally substituted by fluorine, chlorine, cyano, $C_1$–$C_4$-alkoxy, $C_1$–$C_4$-alkylthio, di-($C_1$–$C_4$-alkyl)-amino, Trimethylsilyl, $C_1$–$C_4$-alkoxy-carbonyl, carboxyl, carbamoyl, $C_1$–$C_4$-alkyl-aminocarbonyl, di-($C_1$–$C_3$-alkyl)-aminocarbonyl, or by a heterocyclic grouping as is preferably defined above for $R^1$ (including the possible substituents)), $C_2$–$C_4$-alkenyl (which is optionally substituted by fluorine or chlorine), $C_2$–$C_4$-alkinyl, benzyl (which is optionally substituted by fluorine, chlorine, cyano, nitro, $C_1$–$C_2$alkyl, trifluoromethyl, $C_1$–$C_2$-alkoxy or $C_1$–$C_2$-alkoxycarbonyl), formyl, $C_1$–$C_{20}$-alkyl-carbonyl (which is optionally substituted by fluorine, chlorine, bromine, phenyl, phenoxy or $C_1$–$C_4$-alkoxy), $C_3$–$C_6$-cycloalkylcarbonyl (which is optionally substituted by fluorine, chlorine and/or $C_1$–$C_4$-alkyl), $C_2$–$C_{20}$-alkenyl-carbonyl (which is optionally substituted by fluorine and/or chlorine), phenylcarbonyl or naphthylcarbonyl (which are optionally substituted by fluorine, chlorine, bromine, $C_1$–$C_4$-alkyl, trifluoromethyl, cyano, nitro, $C_1$–$C_4$-alkoxy and/or $C_1$–$C_4$-alkoxy-carbonyl), $C_1$–$C_{20}$-alkoxy-carbonyl, benzyloxycarbonyl, phenoxyarbonyl, $C_1$–$C_4$-alkylthiocarbonyl, benzylthio-carbonyl, phenylthiocarbonyl, $C_1$–$C_6$-alkylamino-carbonyl, di-($C_1$–$C_4$-alkyl)-amino-carbonyl, phenylamino-carbonyl (which is optionally substituted by fluorine, chlorine, bromine, cyano, nitro, $C_1$–$C_4$-alkyl, trifluoromethyl, $C_1$–$C_4$-alkoxy, $C_1$–$C_2$-fluoroalkoxy, $C_1$–$C_2$-chlorofluoroalkoxy, $C_1$–$C_4$-alkylthio, $C_1$–$C_2$-fluoroalkylthio, $C_1$–$C_2$-chlorofluoroalkylthio or $C_1$–$C_4$-alkoxycarbonyl), benzoylamino-carbonyl (which is optionally substituted by fluorine, chlorine, bromine, methyl or trifluoromethyl), phenylsulphonylamino-carbonyl (which is optionally substituted by fluorine, chlorine, bromine, methyl, trifluoromethyl, $C_1$–$C_4$-alkoxy, $C_1$–$C_2$-fluoroalkoxy, $C_1$–$C_2$chlorofluoroalkoxy or $C_1$–$C_4$-alkoxy-carbonyl), $C_1$–$C_4$-alkylthio (which is optionally substituted by fluorine and/or chlorine), phenylthio (which is optionally substituted by fluorine, chlorine, bromine, nitro or methyl), $C_1$–$C_4$-alkylsulphinyl, $C_1$–$C_4$-alkylsulphonyl (which is optionally substituted by fluorine and/or chlorine), phenylsulphinyl (which is optionally substituted by fluorine, chlorine, bromine, nitro or methyl), phenylsulphonyl or naphthylsulphonyl (which are optionally substituted by fluorine, chlorine, bromine, cyano, nitro, methyl, trifluoromethyl, $C_1$–$C_4$-alkoxy, $C_1$–$C_2$-fluoroalkoxy, $C_1$–$C_2$-chlorofluoroalkoxy and/or $C_1$–$C_4$-alkoxycarbonyl), dimethyl(thio)phosphoryl, $C_1$–$C_4$-alkyl-$C_1$–$C_4$-alkoxy-(thio)phosphoryl or di($C_1$–$C_4$-alkoxy)(thio)phosphoryl, Y represents nitrogen or a CH group and Z represents cyano or nitro.

The invention relates, in particular, to compounds of the formula (I) in which $R^1$ represents a five- or six-membered heterocyclic grouping from the series comprising pyrazoyl, 1,2,4-triazolyl, oxazolyl, isoxazolyl, thiazolyl, isothiazolyl, 1,2,5-thiadiazolyl, pyridyl, pyrazinyl and pyrimidinyl, which is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or chlorine), $C_1$–$C_2$-alkylthio (which is optionally substituted by fluorine and/or chlorine) or $C_1$–$C_2$-alkylsulphonyl (which is optionally substituted by fluorine and/or chlorine), $R^2$ represents $C_1$–$C_4$-hydroxyalkyl, dihydroxy-$C_1$–$C_4$-alkyl, $C_1$–$C_3$-alkoxy-$C_1$–$C_3$-alkyl or di-($C_1$–$C_3$-alkoxy)-$C_1$–$C_3$-alkyl, $R^3$ represents hydrogen, $C_1$–$C_4$-alkyl, $C_1$–$C_4$-hydroxyalkyl, dihydroxy-$C_1$–$C_4$-alkyl, $C_1$–$C_3$-alkoxy-$C_1$–$C_3$-alkyl or di($C_1$–$C_3$-alkoxy)-$C_1$–$C_3$-alkyl or $R^2$ and $R^3$ together represent hydroxy-$C_2$–$C_3$-alkanediyl, dihydroxy-$C_2$–$C_3$-alkanediyl, $C_1$–$C_3$-alkoxy-$C_2$–$C_3$-alkanediyl, di-($C_1$–$C_3$-alkoxy)-$C_2$–$C_3$-alkanediyl, oxo- $C_2$–$C_3$-alkanediyl, or dioxo-C2–C3-alkanediyl, $R^4$ represents hydrogen, methyl, ethyl, allyl, propargyl, formyl, $C_1$–$C_8$-alkylcarbonyl (which is optionally substituted by fluorine and/or chlorine), $C_1$–$C_8$-alkoxycarbonyl, benzyloxycarbonyl, Phenoxycarbonyl, benzyl (which is optionally substituted by fluorine or chlorine) or di-($C_1$–$C_2$-alkoxy)-(thio)phosphoryl, Y represents nitrogen or a CH group and Z represents cyano or nitro.

The compounds of the formula (I) are very particularly preferred in which $R^1$ represents 6-chloro-3-pyridyl (6-chloro-pyridin-3-yl) or represents 2-chloro-5-thiazolyl (2-chlorothiazol-5-yl), $R^2$ represents hydroxymethyl, hydroxyethyl, hydroxypropyl, dihydroxyethyl, dihydroxypropyl, methoxymethyl, ethoxymethyl, methoxyethyl, ethoxyethyl, dimethoxyethyl or diethoxyethyl, $R^3$ represents hydrogen, methyl, ethyl, hydroxymethyl, hydroxyethyl, hydroxypropyl, dihydroxyethyl, dihydroxypropyl, methoxymethyl, ethoxymethyl, methoxyethyl, ethoxyethyl, dimethoxyethyl or diethoxyethyl, $R^2$ and $R^3$ together represent oxoethane-1,2-diyl, dioxoethane-1,2-diyl, hydroxyethane-1,2-diyl, dihydroxyethane-1,2-diyl, methoxyethane-1,2-diyl, ethoxyethane-1,2-diyl, dimethoxyethane-1,2-diyl or diethoxyethane-1,2-diyl, $R^4$ represents hydrogen or methyl, Y represents nitrogen or a CH group and Z represents cyano or nitro.

The hydrocarbon radicals, such as alkyl, which are mentioned above in the definition of the compounds of the general formula (I) according to the invention are—also in combination with heteroatoms as in alkoxy—as far as possible in each case straight-chain or branched.

Generally, halogen represents fluorine, chlorine, bromine or iodine, preferably fluorine, chlorine or bromine, in particular fluorine or chlorine.

The above-listed general radical definitions or clarifications, or those listed in the preference ranges, are valid in a corresponding manner for the end products of the formula (I) as well as for the starting compounds and intermediates.

The radical definitions-can be combined together as required, consequently also between the respective preference ranges.

Examples of the compounds of the formula (I) are listed in Table 1 below.

TABLE 1

| Examples of the compounds of the formula (I) | | | | | |
|---|---|---|---|---|---|
| $R^1$ | $R^2$ | $R^3$ | $R^4$ | Y | Z |
| Cl—pyridyl | —CH$_2$CH(OCH$_3$)$_2$ | H | H | N | NO$_2$ |
| Cl—thiazolyl | —CH$_2$CH(OCH$_3$)$_2$ | H | H | N | NO$_2$ |
| Cl—pyridyl | —CH$_2$OH | H | H | N | NO$_2$ |
| Cl—pyridyl | —CH$_2$CH(OCH$_3$)$_2$ | H | CH$_3$ | N | NO$_2$ |
| Cl—pyridyl | —CH$_2$CH$_2$OH | H | H | N | NO$_2$ |
| Cl—pyridyl | —CH$_2$OH | —CH$_2$OH | H | N | NO$_2$ |

TABLE 1-continued

Examples of the compounds of the formula (I)

| R¹ | R² | R³ | R⁴ | Y | Z |
|---|---|---|---|---|---|
| 2-chloropyridin-5-yl | —CH₂CH(OC₂H₅)₂ | H | H | N | NO₂ |
| 2-chlorothiazol-5-yl | —CH₂CH(OC₂H₅)₂ | H | H | N | NO₂ |
| 2-chloropyridin-5-yl | —CH₂CH(OCH₃)₂ | H | H | CH | NO₂ |
| 2-chloropyridin-5-yl | —CH₂CH(OCH₃)₂ | H | H | CH | CN |
| 2-chloropyridin-5-yl | —CH₂CH(OCH₃)₂ | H | H | N | CN |
| 2-chlorothiazol-5-yl | —CH₂CH(OCH₃)₂ | H | H | N | CN |
| 2-chloropyridin-5-yl | —CH(OH)—CH₂— | H | CH | NO₂ | |
| 2-chloropyridin-5-yl | —CH(OH)—CH₂— | H | N | CN | |
| 2-chlorothiazol-5-yl | —CH(OH)—CH(OH)— | H | CH | CN | |
| 2-chloropyridin-5-yl | —CH(OCH₃)—CH₂— | H | N | NO₂ | |
| 2-chloropyridin-5-yl | —CH₂—CH(OCH₃)— | H | CH | NO₂ | |
| 2-chloropyridin-5-yl | —CH(OCH₃)—CH(OCH₃)— | H | N | CN | |
| 2-chlorothiazol-5-yl | —CH(OC₂H₅)—CH₂— | H | CH | NO₂ | |

If, for example, 1-(2-thiazol-5-yl-methyl)-2-cyanoguanidine and chloroacetaldehyde dimethyl acetal are used as starting compounds, the course of the reaction in the process (a) according to the invention can then be represented by the following formula diagram:

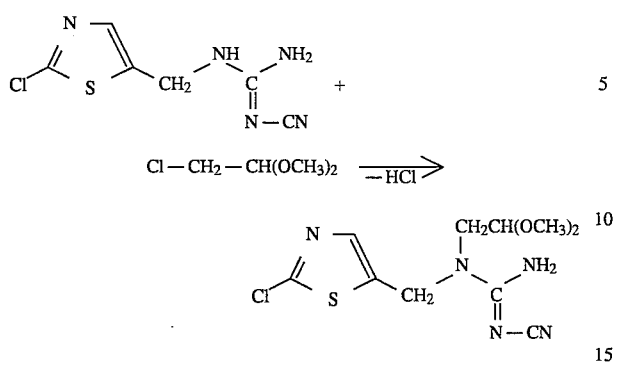

If, for example, 1-(6-chloro-pyridin-3-yl-methyl)-1-(2,2-dimethoxyethyl)-2-nitro-guanidine is used as the starting compound, the course of the reaction in the process (b) according to the invention can then be represented by the following formula diagram:

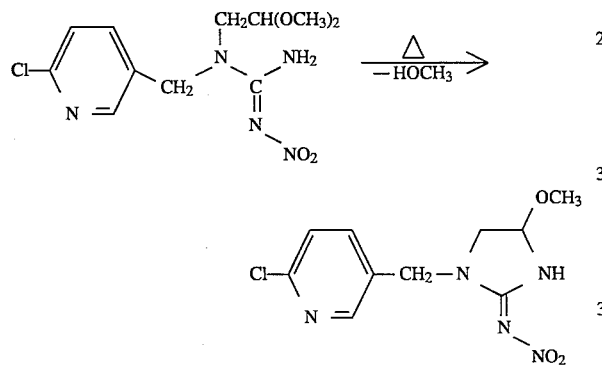

If, for example, 1-(2-chloro-thiazol-5-yl-methyl)-2-nitromethylene-5-oxo-imidazolidine and sodium borohydride are used as the starting compounds, the course of the reaction in the process (c) according to the invention can then be represented by the following formula diagram:

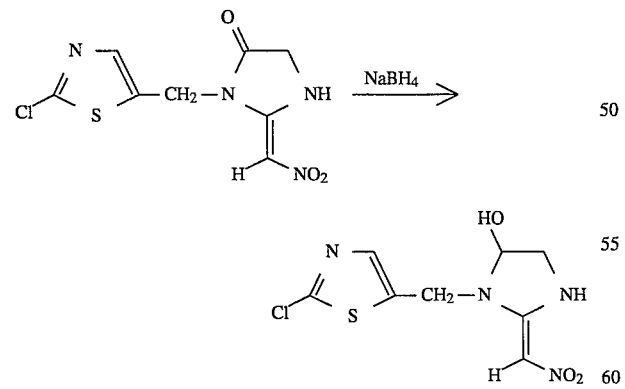

If, for example, 1-(6-chloro-pyridin-3-yl-methyl)-2-cyanomethylene-4-methoxy-imidazoline and hydrogen bromide are used as the starting compounds, the course of the reaction in the process (d) according to the invention can then be represented by the following formula diagram:

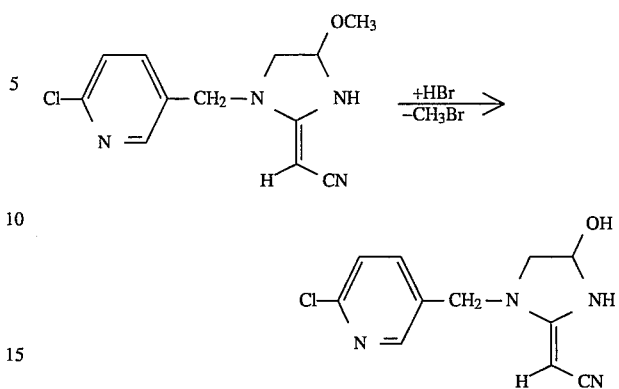

If, for example, 1-(6-chloro-pyridin-3yl-methyl)-2-nitroimino-3-ethyl-5-hydroxy-imidazolidine and ethyl bromide are used as the starting compounds, the course of the reaction in the process (e) according to the invention can then be represented by the following formula diagram:

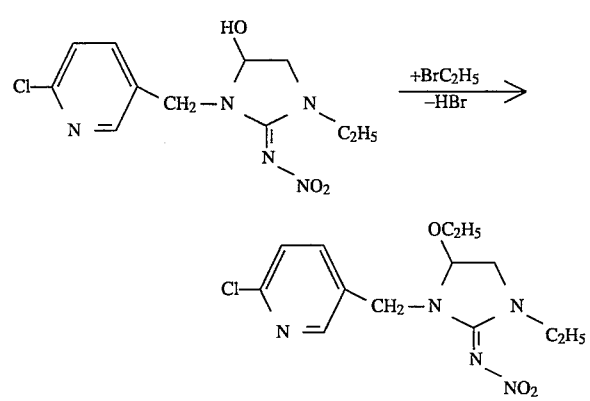

If, for example, 1-(6-chloro-pyridin-3-yl-methyl)-1-(2,2-dimethoxyethyl)-2-nitro-guanidine and methyl bromide are used as the starting compounds, the course of the reaction in the process (f) according to the invention can then be represented by the following formula diagram:

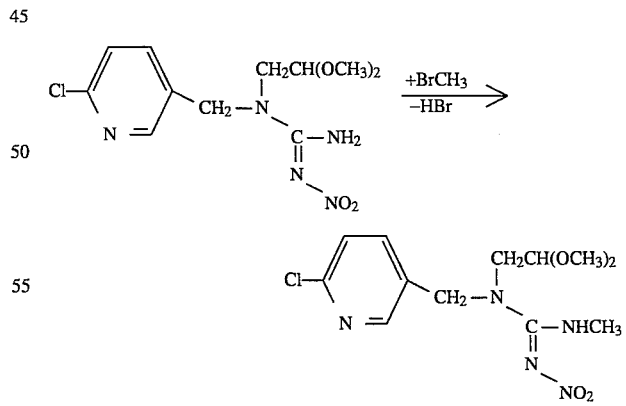

The azoalkanes which are to be used as starting compounds in the process (a) according to the invention for preparing compounds of the formula (I) are generally defined by the formula (II).

In formula (II), $R^1$, Y and Z preferably or in particular have those meanings which have already been indicated above, in connection with the description of the compounds of the formula (I) according to the invention, preferably or as in particular preferred for $R^1$, Y and Z.

The starting compounds of the formula (II) are known and/or can be prepared by processes which are known per se (compare EP-A 302389, EP-A 306696, EP-A 364844, EP-A 375907, EP-A 376297, EP-A 381130, EP-A 418199, EP-A 425978, EP-A 428941, EP-A 452782).

The halogen compounds which are additionally to be used as starting compounds in the process (a) according to the invention for preparing compounds of the formula (1) are generally defined by the formula (IIIa) and the formula (IIIb).

In formula (IIIa) and formula (IIIb), $R^2$ and $R^3$ preferably or in particular have those meanings which have already been indicated above, in connection with the description of the compounds of the formula (I) according to the invention, preferably or as in particular preferred for $R^2$ and $R^3$; X in each case preferably represents chlorine or bromine.

The starting compounds of the formulae (IIIa) and (IIIb) are known chemicals for organic synthesis.

All acid binding agents which are customarily used for reactions of this nature may be employed as acid acceptors in the process (a) according to the invention. Those which are preferably used are alkali metal and alkaline earth metal hydrides, such as lithium, sodium, potassium and calcium hydride, alkali metal and alkaline earth metal hydroxides, such as lithium, sodium, potassium and calcium hydroxide, alkali metal and alkaline earth metal carbonates and hydrogen carbonates, such as sodium and potassium carbonate or hydrogen carbonate, and calcium carbonate, alkali metal acetates, such as sodium and potassium acetate, alkali metal alcoholates, such as sodium and potassium methylate, ethylate, propylate, isopropylate, butylate, isobutylate and tert-butylate, and in addition basic nitrogen compounds, such as trimethylamine, triethylamine, tripropylamine, tributylamine, diisobutylamine, dicyclohexylamine, ethyldiisopropylamine, ethyldicyclohexylamine, ethyldiisopropylamine, ethyldicyclohexylamine, N,N-dimethylbenzylamine, N,N-dimethyl-analine, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

The process (a) according to the invention is optionally carried out in the presence of a catalyst. Suitable catalysts in this context are, in particular, alkali metal salts such as potassium chloride, rubidium chloride and caesium chloride.

The process (a) according to the invention for preparing the novel compounds of the formula (I) is preferably carried out using diluents. In this context, practically all inert organic solvents are suitable diluents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl, methyl isopropyl and methyl isobutyl ketone, esters, such as methyl acetate and ethyl acetate, nitriles, such as, e.g., acetonitrile and propionitrile, amides, such as, e.g., dimethylformamide, dimethylacetamide and N-methylpyrrolidone, as well as dimethyl sulphoxide, tetramethylene sulphone and hexamethylphosphoric triamide.

In the process (a) according to the invention, the reaction temperatures may be varied over a relatively wide range. In general, temperatures of between 0° C. and 200° C., preferably temperatures of between 20° C. and 150° C., are employed.

The process (a) according to the invention is generally carried out under atmospheric pressure. However, it is also possible for it to be carried out under elevated or reduced pressure.

For carrying out the process (a) according to the invention, the starting materials which are required in each case are generally employed in approximately equimolar quantities. However, it is also possible to use one of the two components which are employed in each case in a relatively large excess. The reactions are generally carried out in a suitable diluent in the presence of an acid acceptor and optionally in the presence of a catalyst, and the reaction mixture is stirred for several hours at the temperature which is required in each case. In the process (a) according to the invention, the working up is effected in each case according to customary methods (compare the preparation examples).

The compounds which are to be used as starting compounds in the process (b) according to the invention are generally defined by the formula (I), with the proviso that $R^2$ or $R^3$ represents dialkoxyalkyl. In this case, the radicals $R^1$, $R^2$, $R^3$, $R^4$, Y and Z preferably or in particular have those meanings which have already been indicated above, in the scope of the description of the compounds of the formula (I) according to the invention, preferably or as in particular preferred.

The above-described starting compounds of the formula (I) for process (b) are novel compounds according to the invention; they can be prepared by the process (a) according to the invention.

The process (b) according to the invention is optionally carried out in the presence of a reaction aid. Suitable reaction aids in this context are in particular Lewis acids, such as boron trifluoride or aluminium trichloride, but also mineral acids, such as hydrochloric acid, sulphuric acid, methanesulphonic acid, benzenesulphonic acid and p-toluenesulphonic acid.

The process (b) according to the invention is preferably carried out using a diluent. In this context, those diluents are suitable which have already been mentioned in the description of the process (a) according to the invention. In addition, water, and alcohols, such as methanol, ethanol, n- or i-propanol and n-, i-, s- or t-butanol, can also advantageously be used as diluents in process (b).

In the process (b) according to the invention, the reaction temperatures can be varied over a relatively wide range. In general, temperatures of between 20° C. and 150° C., preferably temperatures of between 40° C. and 100° C., are employed.

The process (b) according to the invention is generally carried out under atmospheric pressure. However, it is also possible for it to be carried out under elevated or reduced pressure.

For carrying out the process (b) according to the invention, the reaction components are generally mixed at room temperature and then stirred at the required temperature until the end of the reaction. The working up can then take place according to customary methods (compare the preparation examples).

The compounds which are to be used as starting compounds in the process (c) according to the invention are generally defined by the formula (I), with the proviso that $R^2$ $R^3$ together represent oxoalkanediyl. In this case, the radicals $R^1$, $R^2$, $R^3$, $R^4$, Y and Z preferably or in particular have those meanings which have already been indicated above, in the scope of the description of the compounds of the formula (I) according to the invention, preferably or as in particular preferred.

The above-described starting compounds of the formula (I) for process (c) are novel compounds according to the invention; they can be prepared by the process (a) according to the invention.

The process (c) according to the invention is carried out using a hydrogenating agent. Appropriate agents in this context are, in particular, the metal hydride complexes, such as lithium borohydride (LiBH$_4$), lithium aluminium hydride (LiAlH$_4$) and sodium borohydride (NaBH$_4$), which are suitable for hydrogenating carbonyl compounds to hydroxy compounds.

Process (c) is optionally carried out in the presence of a reaction aid. Suitable reaction aids in this context are, in particular, acids, such as hydrochloric acid, sulphuric acid or acetic acid.

Process (c) is preferably carried out using a diluent. In this context, those diluents are preferably suitable which have already been mentioned in the description of the process (a) according to the invention. In addition, water, alcohols, such as methanol, ethanol, n- and i-propanol, and additionally also carboxylic acids, such as acetic acid and propionic acid, can also advantageously be used as diluents in process (c).

In the process (c) according to the invention, the reaction temperatures may be varied over a relatively wide range. In general, temperatures of between −20° C. and +50° C., preferably temperatures of between 0° C. and +30° C., are employed.

The process (c) according to the invention is generally carried out under atmospheric pressure. However, it is also possible to carry it out under elevated or reduced pressure.

For carrying out the process (c) according to the invention, the starting compounds which are required in each case are generally employed in approximately equimolar quantities. However, it is also possible to use one of the two components employed in each case in a relatively large excess. The reactions are generally carried out in a suitable diluent in the presence of a reaction aid, and the reaction mixture is stirred at the temperature which is required in each case. The working up in the process (c) according to the invention is effected in each case according to customary methods (compare the preparation examples).

The compounds which are to be used as starting compounds in the process (d) according to the invention are generally defined by the formula (I), with the proviso that R$^2$ and R$^3$ together represent akoxyalkanediyl or dialkoxyalkanediyl. In this case, the radicals R$^1$, R$^2$, R$^3$, R$^4$, Y and Z preferably or in particular have those meanings which have already been indicated above, in the scope of the description of the compounds of the formula (I) according to the invention, preferably or as in particular preferred.

The above-described starting compounds of the formula (I) for process (d) are novel compounds according to the invention; they can be prepared by the processes (a) or (b) according to the invention.

The process (d) according to the invention is carried out in the presence of a hydrogen halide and/or an alkali metal halide. Preferably, hydrogen chloride or hydrogen bromide, and/or corresponding sodium or potassium halides, that is sodium or potassium chloride or bromide, are employed.

Process (d) is preferably carried out using a diluent. Besides water, those diluents are preferably suitable in this context which have already been mentioned in the description of the process (a) according to the invention.

In the process (d) according to the invention, the reaction temperatures can be varied over a relatively wide range. In general, temperatures of between 0° C. and 100° C., preferably temperatures of between 20° C. and 80° C., are employed.

The process (d) according to the invention is generally carried out under atmospheric pressure. However, it is also possible to carry it out under elevated or reduced pressure.

For carrying out the process (d) according to the invention, the starting materials which are required in each case are generally employed in approximately equimolar quantities. However it is also possible to use one of the two components which are employed in each case in a relatively large excess. The reactions are generally carried out in a suitable diluent, and the reaction mixture is stirred for several hours at the temperature which is necessry in each case. The working up in the process (d) according to the invention is in each case effected according to customary methods (compare the preparation examples).

The compounds which are to be used as starting compounds in the process (e) according to the invention are generally defined by the formula (I), with the proviso that R$^2$ and R$^3$ together represent hydroxyalkanediyl or dihydroxyalkanediyl. In this case, the radicals R$^1$, R$^2$, R$^3$, R$^4$, Y and Z preferably have those meanings which have already been indicated above, in the scope of the description of the compounds of the formula (I) according to the invention, preferably or as in particular preferred.

The above-described starting compounds of the formula (I) for process (e) are novel compounds according to the invention; they can be prepared by the processes (c) or (d) according to the invention.

The alkylating agents which are additionally to be used as starting compounds in the process (e) according to the invention for preparing compounds of the formula (I) are generally defined by the formula (IV).

In formula (IV)

R preferably represents C$_1$–C$_4$-alkyl, in particular methyl or ethyl, and

X preferably represents chlorine, bromine or iodine, or the grouping -O-SO$_2$-O R, in which R has the above-mentioned meaning.

The starting compounds of the formula (IV) are known chemicals for organic synthesis.

The process (e) according to the invention is preferably carried out in the presence of an acid acceptor. In this context, those acid binding agents are preferably suitable which have been mentioned above in the description of the process (a) according to the invention.

The process (e) according to the invention is preferably carried out using a diluent. In this context, those diluents are preferably suitable which have been mentioned above in the description of the process (a) according to the invention.

In the process (e) according to the invention, the reaction temperatures can be varied over a relatively wide range. In general, temperatures of between 0° C. and 150° C., preferably temperatures of between 20° C. and 100° C., are employed.

The process (e) according to the invention is generally carried out under atmospheric pressure. However, it is also possible to carry it out under elevated or reduced pressure.

For carrying out the process (e) according to the invention, the starting compounds which are required in each case are generally employed in approximately equimolar quantities. However, it is also possible to use one of the two components which are employed in each case in a relatively large excess. The reactions are generally carried out in a suitable diluent in the presence of an acid acceptor, and the reaction mixture is stirred for several hours at the temperature which is necessary in each case. The working up in the process (e) according to the invention is in each case effected according to customary methods (compare the preparation examples).

The compounds to be used as starting compounds in the process (f) according to the invention are generally defined by the formula (I), with the proviso that $R^4$ represents hydrogen In this case, the radicals $R^1$, $R^2$, $R^3$, Y and Z preferably or in particular have those meanings which have already been indicated above, in the scope of the description of the compounds of the formula (I) according to the invention, preferably or as in particular preferred.

The above-described starting compounds of the formula (I) for process (f) are novel compounds according to the invention; they can be prepared by the processes (a) to (d) according to the invention.

The halogen compounds which are additionally to be used as starting compounds in the process (f) according to the invention for preparing compounds of the formula (I) are generally defined by the formula (V).

In formula (V), $R^4$ preferably or in particular has that meaning which has already been indicated above, in connection with the description of the compounds of the formula (I) according to the invention, preferably or as in particular preferred for $R^4$;

X preferably represents fluorine, chlorine, bromine or iodine, in particular chlorine or bromine.

The starting compounds of the formula (V) are known chemicals for organic synthesis.

The process (f) according to the invention is preferably carried out in the presence of an acid acceptor. In this context, those acid binding agents are preferably suitable which have been mentioned above in the description of the process (a) according to the invention.

The process (f) according to the invention is preferably carried out using a diluent. In this context, those diluents are preferably suitable which have been mentioned above in the description of the process (a) according to the invention.

In the process (f) according to the invention, the reaction temperatures can be varied over a relatively wide range. In general, temperatures of between 0° C. and 150° C., preferably temperatures of between 20° C. and 100° C., are employed. The process (f) according to the invention is generally carried out under atmospheric pressure. However, it is also possible to carry it out under elevated or reduced pressure.

For carrying out the process (f) according to the invention, the starting compounds which are required in each case are generally employed in approximately equimolar quantities. However, it is also possible to use one of the two components which are employed in each case in a relatively large excess. The reactions are generally carried out in a suitable diluent in the presence of an acid acceptor, and the reaction mixture is stirred for several hours at the temperature which is required in each case. The working up in the process (f) according to the invention is in each case effected according to customary methods.

While being well-tolerated by plants and having favourable toxicity to warm-blooded animals, the active compounds are suitable for controlling animal pests, in particular insects, arachnida and nematodes, which are encountered in agriculture, in forestry, in the protection of stored products and of materials, and in the hygiene field. They are active against normally sensitive and resistant species and against all or individual stages of development. The abovementioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis*, *Periplaneta americana*, *Leucophaea maderae*, *Blattella germanica*, *Acheta domesticus*, Gryllotalpa spp., *Locusta migratoria migratorioides*, *Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius*, *Piesma quadrata*, *Cimex lectularius*, *Rhodnius prolixus* and Triatoma spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, Myzus spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, Pseudococcus spp. Psylla spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, Lymantria spp. *Bucculatrix thurberiella*, *Phyllocnistis citrella*, Agrotis spp., Euxoa spp., Feltia spp., *Earias insulana*, Heliothis spp., *Laphygma exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima* and *Tortrix viridana*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*,

*Ceuthorhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp.

The active compounds of the formula (I) according to the invention are distinguished by outstanding insecticidal activity. They exhibit a very strong action both as leaf insecticides and as ground insecticides, e.g. against beetle larvae (e.g. *Phaedon cocheariae*), against rice leaf hoppers (e.g. *Nephotettix cincticeps*) and against leaf aphids (e.g. *Myzus persicae* and *Aphis fabae*).

The active compounds of the formula (I) according to the invention are also suitable for combating arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice. By combating these anthropods cases of death and reductions in productivity (for meat, milk, wool, hides, eggs, honey etc.) should be diminished, so that a more economic and simpler animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intra-muscular, by nasal administration, by dermal use in the form, for example, of dipping or bathing, spraying, pouring on and spotting on), washing and powdering, and also with the aid of shaped articles containing the active compound, such as collars, ear tags, tail tags, limb bands, halters, marking devices, etc.

Depending on their particular phydical and/or chemical oak shafts, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, an optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxy-methylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content, of the use forms prepared from the commercially available formulations, can vary within wide limits. The active compound concentration of the use forms can be from 0.0000001 to 95% by weight of active compound, preferably between 0.0001 and 1% by weight.

Application is effected in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

EXAMPLE 1

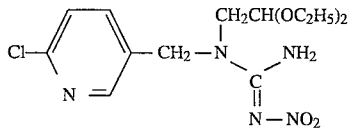

<Process (a)>

A mixture of 1.15 g (5.0 mmol) of 1-(6-chloro-pyridin-3-yl-methyl)-2-nitroguanidine, 0.76 g (5.5 mmol) of potassium carbonate, 0.09 g (0.5 mmol) of caesium chloride, 0.92 ml (5.5 mmol) of bromoacetaldehyde diethyl acetal and 5 ml of dimethylformamide is heated to 125° C. while stirring, and stirred at this temperature for two hours. After the addition of a further 0.76 g (5.5 mmol) of potassium carbonate and a further 0.92 ml (5.5 mmol) of bromoacetaldehyde diethyl acetal, the mixture is stirred at 125° C. for a further two hours.

After cooling to room temperature, the mixture is then diluted with ice water to about four times the volume, and extracted with methylene chloride. The organic phase is dried with sodium sulphate, and filtered. The filtrate is concentrated and the residue is digested with ice-cold cyclohexane. The syrupy crude product which remains undissolved during this process is purified by column chromatography (silica gel; methylene chloride /ethyl acetate 1:1).

0.16 g (9% of theory) of 1-(6-chloro-pyridin-3-yl-methyl)- 1-(2,2-diethoxyethyl)-2-nitro-guanidine are thus obtained as an amorphous 2nd fraction.

$^1$H-NMR (CDCl$_3$,δ): —CH(OC$_2$H$_5$)$_2$ 4.59 ppm (triplet) —CH$_2$—CH(OC$_2$H$_5$)$_2$ 3.39 ppm (doublet)

EXAMPLE 2

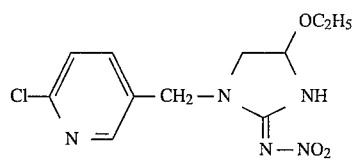

<Process (b)>

A mixture of 1.45 g (4.2 mmol) of 1-(6-chloro-pyridin-3-yl-methyl)- 1-(2,2-diethoxy-ethyl)-2-nitro-guanidine and 44 ml of ethanol is heated to 78° C. and, after the addition of 0.725 ml (7.25 mmol) of concentrated hydrochloric acid, is stirred at this temperature for 15 minutes.

After cooling to room temperature, the mixture is diluted with ethyl acetate to about three times the volume, and neutralised with aqueous potassium hydrogen carbonate solution. The organic phase is separated off, dried with sodium sulphate and filtered. The filtrate is concentrated and the residue is purified by column chromatography (silica gel; methylene chloride/methanol 15:1). 1.2 g (95% of theory) of 1-(6-chloro-pyridin-3-yl-methyl)-2-nitroimino- 4-ethoxy-imidazolidine are obtained as an amorphous 2nd fraction.

$^1$H-NMR (DMSO$_3$, δ): 4—CH 5.90 ppm 5—CH$_2$ 3.70 ppm (multiplet)

EXAMPLE 3

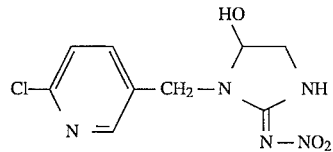

<Process (c)>

4.2 g (15.5 mmol) of 1-(6-chloro-pyridin-3-yl-methyl)-2-nitroimino-5-oxo-imidazolidine are dissolved in 495 ml of tetrahydrofuran, and 25.2 ml (25.2 mmol of HCl) of 1N hydrochloric acid are then added to this solution. The mixture is cooled to 15° C., and 42 ml of a 4% strength aqueous solution of sodium borohydride are added dropwise to it at this temperature. After stirring subsequently for 30 minutes, the solution is decanted off from the undissolved solid and concentrated. 200 ml of saturated aqueous sodium chloride solution are then added, and the mixture is extracted three times with 200 ml of ethyl acetate on each occasion.

The combined organic phases are dried with sodium sulphate and filtered. The filtrate is concentrated, the residue is digested with 200 ml of ethyl acetate/acetonitrile (10:1), and the product which remains undissolved is isolated by filtering off with suction.

1st product fraction: 0.6 g of brown-yellow crystals. The filtrate is fractionated on a silica gel column. 2nd product fraction: 2.8 g of colourless crystals; Melting point: 192° C. Total yield: 3.4 g (80% of theory) of 1-(6-chloro-pyridin-3-yl-methyl) 2-nitroimino-5-hydroxy-imidazolidine.

EXAMPLE 4

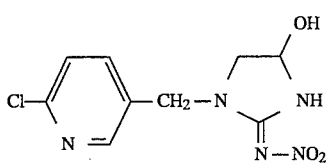

<Process (d)>

A mixture of 0.36 g (1.2 mmol) of 1-(6-chloro-pyridin 3-yl-methyl-2-nitroimino-4-ethoxy-imidazolidine, 36 ml of tetrahydrofuran, 36 ml of saturated aqueous sodium chloride solution and 2.4 ml of 1N hydrochloric acid is stirred at 45° C. for 105 minutes.

After cooling to room temperature, the two-phase reaction mixture is adjusted to pH 8 using potassium hydrogen carbonate solution, and is then extracted three times with ethyl acetate. The combined extracts are dried with sodium sulphate and filtered. The filtrate is concentrated, the residue is digested with diethyl ether, and the resultant crystalline product is isolated by filtration with suction.

0.143 g (44% of theory) of 1-(6-chloro-pyridin-3-yl-methyl)- 2-nitroimino-4-hydroxy-imidazolidine are obtained with a melting point of 170° C.

EXAMPLE 5

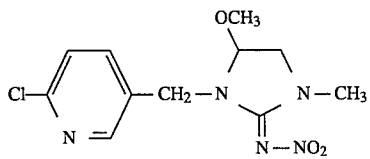

<Process (e)>

1.1 g (4.0 mmol) of 1-(6-chloro-pyridin-3-yl-methyl)-2-nitroimino- 5-hydroxy-imidazolidine are dissolved in 10 ml of dimethylformamide, and 0.24 g (8.0 mmol) of sodium hydride are then added in portions to this solution while stirring. The mixture is stirred at 15° C. for 30 minutes. 0.5 ml (8.0 mmol) of methyl iodide are then added dropwise at +5° C. and the reaction mixture is stirred at 20° C. for 2 hours. Subsequently, the mixture is diluted with water to about three times the volume, and then extracted three times with ethyl acetate. The combined extracts are dried with sodium sulphate and filtered. The filtrate is concentrated and the residue is fractionated by column chromatography (silica gel | ethyl acetate).

0.80 g (67% of theory) of 1-(6-chloro-pyridin-3-yl-methyl)- 2-nitroimino-3-methyl-5-methoxy-imidazolidine are obtained as an amorphous 3rd fraction. $^1$H-NMR(CDCl$_3$,) OCH$_3$ 3.26 ppm (singlet) NCH$_3$ 3.01 ppm (singlet)

The compounds of the formula (I) listed in Table 2 below can also, for example, be prepared in analogy with the Preparation Examples 1 to 5 and in accordance with the general description of the preparation processes according to the invention.

TABLE 2

| Ex. No.: | R$^1$ | R$^2$ | R$^3$ | R$^4$ | Y | Z | Physical Data |
|---|---|---|---|---|---|---|---|
| 6 | Cl-pyridyl | —C(O)—CH$_2$— | | H | N | NO$_2$ | m.p.: 173° C. |
| 7 | Cl-pyridyl | —CH(OH)—CH(OH)— | | H | N | NO$_2$ | m.p.: 185° C. |
| 8 | Cl-pyridyl | —CH$_2$CH(OC$_2$H$_5$)$_2$ | —CH$_2$CH(OC$_2$H$_5$)$_2$ | H | N | NO$_2$ | (amorph.) |
| 9 | Cl-pyridyl | —CH$_2$CH(OCH$_3$)$_2$ | H | H | N | NO$_2$ | (amorph.) |
| 10 | Cl-pyridyl | —CH$_2$—CH(OCH$_3$)— | | H | N | NO$_2$ | (amorph.) |

TABLE 2-continued

Preparation examples for the compounds of the formula (I)

| Ex. No.: | R¹ | R² | R³ | R⁴ | Y | Z | Physical Data |
|---|---|---|---|---|---|---|---|
| 11 | 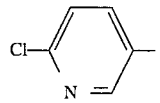 | | $-CH_2-\underset{\underset{OCH_3}{\mid}}{CH}-$ | $CH_3$ | N | $NO_2$ | (amorph.) |
| 12 | 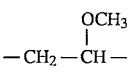 | | (cis) $-\underset{\underset{OCH_3}{\mid}}{CH_2}-\underset{\underset{OCH_3}{\mid}}{CH_2}-$ | H | N | $NO_2$ | m.p.: 127° C. |
| 13 | 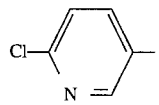 | | (trans) $-\underset{\underset{OCH_3}{\mid}}{CH}-\underset{\underset{OCH_3}{\mid}}{CH}-$ | H | N | $NO_2$ | (amorph.) |

Application Examples

Example A

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the desired time, the destruction in % is determined. 100% means that all the beetle larvae have been killed; 0% means that none of the beetle larvae have been killed.

In this test, the compounds obtained according to the Preparation Examples (1), (3), (5) and 6), for example, exhibit, at a concentration of active compound of 0.1%, a 100% destruction of the test animals after 7 days.

Example B

Nephotettix test

Solvent 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (Oryza sativa) are treated by being dipped into the preparation of the active compound of the desired concentration and are infested with larvae of the green rice leafhopper (Nephotettix cincticeps), as long as the seedlings are still moist.

After the desired time, the destruction in % is determined. 100% means that all the leafhoppers have been killed; 0% means that none of the leafhoppers has been killed.

In this test, the compounds obtained according to the Preparation Examples (1), (3), (5) and (8), for example, exhibit, at a concentration of active compound of 0.1%, a 100% destruction of the test animals after 6 days.

Example C

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*), which are strongly infested with the green peach aphid (*Myzus persicae*), are treated by being dipped into the preparation of the active compound of the desired concentration.

After the desired time, the destruction in % is determined. 100% means that all the test insects have been killed; 0% means that none of the aphids has been killed.

In this test, the compounds obtained according to the Preparation Examples (1) and (5), for example, exhibit, at a concentration of active compound of 0.1%, a 100% destruction of the test animals after 6 days.

Example D

Aphis test (systemic action)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which have been heavily infested with the black bean aphid (*Aphis fabae*) are each watered with 20 ml of the preparation of the active compound of the desired concentration in such a way that the preparation of the active compound penetrates into the soil without wetting the shoot. The active compound is taken up by the roots and passed to the shoot.

After the desired time, the destruction in % is determined. 100% means that all the test insects have been killed; 0% means that none of the test insects has been killed.

In this test, the compounds obtained according to the Preparation Examples (3) and (5), for example, exhibit, at a concentration of active compound of 0.1%, a 100% destruction of the test animals after 4 days.

Example E

Critical concentration test / root-systemic action

Test insect: *Myzus persicae*

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg1), being decisive. The treated soil is transferred into pots and these are planted with cabbage (Brassica oleracea). The active compound can in this way be taken up from the soil by the roots of the plants and be transported into the leaves.

To demonstrate the root-systemic effect, the leaves are infested with the abovementioned test insects after 7 days. After a further 2 days, the evaluation is made by counting or estimating the dead insects The root-systemic action of the active compound is deduced from the mortality figures. It is 100% if all test animals have been killed and 0% if just as many test insects are still alive as in the case of the untreated control.

In this test, the compounds obtained according to the Preparation Examples (1) and (3), for example, exhibit, at a concentration of active compound of 20 ppm, a 100% destruction of the test animals.

Example F

Blowfly larvae test

Test animals: *Lucilia cuprina* larvae

Emulsifier: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture, and the emulsion concentrate thus obtained is diluted with water to the desired concentration in each case.

About 20 *Lucilia cuprina* res. *larvae* are placed in a test tube, which contains about 1 cm³ of horse meat and 0.5 ml of the preparation of the active compound. After 24 hours, the effectiveness of the preparation of the active compound is determined. 100% means that all the blowfly larvae have been killed; 0% means that no blowfly larvae have been killed.

In this test, the compounds according to the Preparation Examples (1), (2), (4), (5) and (8), for example, exhibit good effectiveness.

We claim:

1. Substituted diazacycloalkanes of the formula (I)

$$R^1 \diagdown_{N}^{R^2} \diagup^{R^3}_{N-R^4}$$
$$\underset{Z}{\overset{Y}{\|}}$$

(I)

in which $R^1$ represents a five- or six-membered heterocyclic grouping which contains 1, 2, 3 or 4 nitrogen atoms and/or one or two oxygen atoms or sulphur atoms as the heteroatom ring members—the number of heteroatoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, arylthio, arylamino, aralkyl, formylamino, alkylcarbonylamino, formyl, carbamoyl, alkyl-carbonyl and/or alkoxycarbonyl, $R^2$ and $R^3$ together represent hydroxyethanediyl, dihydroxyethanediyl, alkoxyethanediyl, dialkoxyethanediyl, oxoethanediyl or dioxoethanediyl, $R^4$ represents hydrogen, alkyl (which is optionally substituted by halogen, cyano, alkoxy, alkylthio, dialkylamino, trialkylsilyl, alkoxycarbonyl, carboxyl, carbamoyl, alkylaminocarbonyl or dialkylaminocarbonyl, or by the radical $R^1$, where $R^1$ has the above mentioned meaning), alkenyl (which is optionally substituted by halogen), alkinyl, benzyl (which is optionally substituted by halogen, cyano, nitro, alkyl, halogenoalkyl, alkoxy or alkoxycarbonyl), formyl, alkylcarbonyl (which is optionally substituted by halogen, cyano, phenyl, phenoxy or alkoxy), cycloalkylcarbonyl (which is optionally substituted by at least one of halogen and alkyl), alkenylcarbonyl (which is optionally substituted byhalogen), phenyl-carbonyl or naphthylcarbonyl (which are optionally substituted by at least one of halogen, alkyl, halogenoalkyl, cyano, nitro, alkoxy and alkoxy-carbonyl), alkoxycarbonyl, benzyloxycarbonyl, phenoxycarbonyl, alkylthiocarbonyl, benzylthio-carbonyl, phenythiocarbonyl, alkylaminocarbonyl, dialkylaminocarbonyl, phenylaminocarbonyl (which is optionally substituted by halogen, cyano, nitro, alkyl, halogenoalkyl, alkoxy, halogenoalkoxy, alkylthio, halogenoalkylthio or alkoxycarbonyl), benzoylaminocarbonyl (which is optionally substituted by halogen, alkyl or halogenoalkyl), phenylsulphonylaminocarbonyl (which is optionally substituted by halogen, alkyl, halogenoalkyl, alkoxy, halogenoalkoxy or alkoxy-carbonyl), alkylthio (which is optionally substituted by halogen), phenylthio (which is optionally substituted by halogen, nitro or alkyl), alkylsulphinyl, alkylsulphonyl (which is optionally substituted by halogen), phenyl-sulphinyl (which is optionally substituted by halogen, nitro or alkyl), phenylsulphonyl or naphthylsulphonyl (which are optionally substituted by at least one of halogen, cyano, nitro, alkyl, halogenoalkyl, alkoxy, halogenoalkoxy and alkoxycarbonyl), dialkyl(thio)phosphoryl, alkylalkoxy-(thio) phosphoryl or dialkoxy-(thio)phosphoryl, Y represents nitrogen or a CH group and Z represents cyano or nitro.

2. Substituted diazacycloalkanes of the formula (I)

according to claim 1, in which

R$^1$ represents a five- or six-membered heterocyclic grouping from the series comprising pyrazoyl, 1,2,4-triazolyl, oxazolyl, isoxazolyl, thiazolyl, isothiazolyl, 1,2,5-thiadiazolyl, pyridyl, pyrazinyl and pyrimidinyl, which is optionally substituted by fluorine, chlorine, bromine, cyano, nitro, C$_1$–C$_2$-alkyl (which is optionally substituted by fluorine and/or chlorine), C$_1$–C$_2$-alkoxy (which is optionally substituted by fluorine and/or chlorine), C$_1$–C$_2$-alkylthio (which is optionally substituted by fluorine and/or chlorine) or C$_1$–C$_2$-alkylsulphonyl (which is optionally substituted by fluorine and/or chlorine), R$^2$ and R$^3$ together represent hydroxyetanediyl, dihydroxyethanediyl, C$_1$–C$_3$-alkoxyethanediyl, di-(C$_1$–C$_3$-alkoxy)-ethanediyl, oxo-ethanediyl or dioxo-ethanediyl, R$^4$ represents hydrogen, methyl, ethyl, allyl, propargyl, formyl, C$_1$–C$_8$-alkylcarbonyl (which is optionally substituted by fluorine and/or chlorine), C$_1$–C$_8$-alkoxy carbonyl, benzyloxycarbonyl, phenoxycarbonyl, benzyl (which is optionally substituted by fluorine or chlorine) or di-(C$_1$–C$_2$-alkoxy)-(thio)phosphoryl, Y represents nitrogen or a CH group and Z represents cyano or nitro.

3. Substituted aza(cyclo)alkanes of the formula (I) according to claim 1, in which R$^1$ represents 6-chloro-3-pyridyl or represents 2-chloro-5-thiazolyl, R$^2$ and R$^3$ together represent oxoethane-1,2-diyl, dioxoethane-1,2-diyl, hydroxyethane-1,2-diyl, dihydroxyethane-1,2-diyl, methoxyethane-1,2-diyl, ethoxyethane-1,2-diyl, dimethoxyethane-1,2-diyl or diethoxyethane-1,2-diyl, R$^4$ represents hydrogen or methyl, Y represents nitrogen or a CH group and Z represents cyano or nitro.

4. An insecticidal composition comprising an insecticidally effective amount of a compound according to claim 1 and a carrier.

5. A method of combating insects which comprises applying to such insects or to an insect habitat an insecticidally effective amount of a compound according to claim 1 and a carrier.

* * * * *

UNITED STATES PATENT AND TRADEMARK OFFICE
CERTIFICATE OF CORRECTION

PATENT NO. : 5,461,069
DATED : October 24, 1995
INVENTOR(S) : Wagner, et al.

It is certified that error appears in the above-indentified patent and that said Letters Patent is hereby corrected as shown below:

Title Page      FOREIGN PATENT DOCUMENTS: Delete " 0302339 " and substitute -- 0302389 --

Col. 26, line 45      Delete " phenythiocarbonyl " and substitute -- phenylthiocarbonyl --

Signed and Sealed this

Thirtieth Day of January, 1996

Attest:

BRUCE LEHMAN

Attesting Officer      Commissioner of Patents and Trademarks